United States Patent [19]

Dewar et al.

[11] Patent Number: 4,977,015

[45] Date of Patent: Dec. 11, 1990

[54] FILMS AND TAPES

[75] Inventors: Colin A. Dewar, Hucclecote; Kevin J. Artus, Barnwood, both of United Kingdom

[73] Assignee: Imperial Chemical Industries PLC, London, England

[21] Appl. No.: 454,910

[22] Filed: Dec. 22, 1989

Related U.S. Application Data

[62] Division of Ser. No. 167,160, Mar. 11, 1988, Pat. No. 4,919,996.

[30] Foreign Application Priority Data

Mar. 17, 1987 [GB] United Kingdom ............... 8706274

[51] Int. Cl.$^5$ ............................................. B32B 3/00
[52] U.S. Cl. .................................... 428/221; 428/225; 428/297
[58] Field of Search ............... 428/910, 221, 296, 297, 428/131, 225

[56] References Cited

U.S. PATENT DOCUMENTS 4,755,540 7/1988 Blakey ................................... 521/62
4,842,924 6/1989 Farris et al. ......................... 428/910

FOREIGN PATENT DOCUMENTS 0164235 12/1985 European Pat. Off. .
0080274 5/1986 European Pat. Off. .
1268861 3/1972 United Kingdom .
1309295 3/1973 United Kingdom .

OTHER PUBLICATIONS

Maxwell et al., *Polymer Engineering and Science*, vol. 23, No. 11, Mid-Aug. 1983.
Japanese Abstracts of Patent Nos. 105967 and 103517.

*Primary Examiner*—James J. Bell
*Attorney, Agent, or Firm*—Cushman, Darby & Cushman

[57] ABSTRACT

A melt spun film or tape of a thermoplastic fibre-forming polymer comprising spaced fibrils of the polymer which are substantially aligned to the longitudinal axis of the film, such aligned, spaced fibrils being interconnted to each other in a random manner.

2 Claims, No Drawings

FILMS AND TAPES

This invention relates to melt spun films and tapes of a thermoplastic fibre-forming polymer.

According to the present invention we provide a melt spun film or tape of a thermoplastic fibre-forming polymer comprising spaced fibrils of the polymer which are substantially aligned to the longitudinal axis of the film, such aligned, spaced fibrils being interconnected to each other in a random manner.

We have found that a film or tape can be produced by forming a blend of the polymer and another thermoplastic, film-forming polymer by melt spinning the blend and then leaching away the other polymer using a suitable solvent leaving a low density, porous, film or tape according to the invention.

The structure of the blend at spinning was determined by examination of the extrudate upon exit from the spinneret. This was sectioned and examined under the microscope. Usually melt blends of two immiscible polymers produce a two phase system where one polymer forms the continuous phase and the other the discontinuous phase, which appears as globules in the extrudate. When the film or tape is spun, the globules, if they have a suitable viscosity, deform into individual fibrils which are not connected to each other.

For certain blend compositions and spinning conditions we have found that an interpenetrating network (IPN) of the two polymers can be formed where both polymeric phases are co-continuous. Each polymer is in the form of a three dimensional network which interlocks with the other polymer network. In the spun film or tape this mutual interlocking is maintained, each polymer being present in the film or tape as oriented fibrils which are substantially aligned to the longitudinal axis of the film or tape such aligned fibrils being interconnected to each other in a random manner, such interconnections penetrating through the fibrils of the other polymer.

To produce such a film or tape two conditions are necessary: (1) the blend must form an IPN and (2) this IPN must be spinnable by which we mean that the film or tape produced therefrom is capable of being wound up. There is only a limited range of conditions for a particular two component polymer system where an IPN can be formed and, moreover, even when operating within that range of conditions the two component polymer system may not always be spinnable. When the blend is unspinnable the film or tape breaks continuously on withdrawal from the spinneret.

A critical condition for the formation of an IPN is the degree of shear imparted to the polymer system during spinning. This shear is dependent on various factors such as the size of the spinneret orifice, its shape and length to diameter ratio. Total strain is also important. Another factor is the relative concentrations of the two polymers.

According to the method of the invention, therefore, a blend of a first thermoplastic fibre-forming polymeric component and a second, immiscible, thermoplastic fibre-forming polymeric component and containing from 30 to 70 parts by weight of the first polymer and from 70 to 30 parts by weight of the second polymer is spun under those conditions of shear which results in each component being present in the film or tape as fibrils which are substantially aligned to the longitudinal axis of the film or tape, such aligned fibrils of one polymeric component being interconnected to each other in a random manner, such interconnections penetrating through the fibrils (of the other polymeric component such that both components exist in the film or tape as interpenetrating networks, and then, using a suitable solvent, leaching away from the film or tape the second fibre-forming polymer leaving a low density, porous film or tape of the first fibre-forming polymer.

Though the invention can be readily carried out with the more conventional fibre-forming polymers such as nylon, polyethylene terephthalate, polypropylene and polyurethane we have found it particularly useful with those polymers containing aromatic repeat units in the chain, such as polysulphones, polyethersulphones, polyetherethersulphones, polyetherketones, polyetheretherketones, polyarylene oxides, polyarylene sulphides aromatic polyamides, aromatic polyesters, aromatic polycarbonates, polyetherimides.

Films or tapes of such materials produced in accordance with the invention may be modified to show specific physical properties, depending upon the conditions used and the presence or absence of a compatibiliser at specified levels. The invention will now be described with reference to the following Examples. In these examples a small screw extruder was used. Any suitable slot die may be used in the spinning process.

EXAMPLE 1

A blend was formed between 65 parts by weight of polyether sulphone ("Victrex" PES 3600 g ex ICI) which had been dried under vacuum for 5 hours at 150° C. and 35 parts by weight of polyethylene (BP 45).

The blend was spun at a temperature of 325° C. through a slot die at 16.4 grams/minute to produce a tape 4 mm wide. The tape was quenched using a conventional air quench.

Samples of the tape were immersed in 100 cc of boiling petroleum ether in a flask for 45 minutes. The solution was decanted off and replenished with 100 cc of petroleum ether and boiled for a further 60 minutes.

Substantially all of the polyethylene had been extracted from the tape leaving a pliant, integral structure comprising fibrils of polyether sulphone, highly connected but substantially aligned to the axis of spinning.

Such a tape, being pliable, is particularly useful as a seal for valves and pipe joints. A conventionally produced tape of equivalent thickness would be expected to exhibit a higher modulus so rendering it less conformable and ill suited for this purpose.

Furthermore because of their thermal and chemical resistance, tapes made form polyether sulphone or other polyaromatic polymers are particularly suited for this purpose.

EXAMPLE 2

A blend was formed between 65 parts by weight of a polyether based polyurethane ("Estane" 58300 ex BF Goodrich) which had been dried under Nitrogen bleed vacuum for four hours at 45° C. and 35 parts by weight of polypropylene. ("Propathene" PXC 31631).

The blend was spun at a temperature of 190° C. through a slot die, 3.4 mm long and 150µ wide to give a tape of 7 mm width and 650µ wide with a throughput of 4.35 g/min. The tape was stiff and translucent. The tape was quenched using a conventional air quench.

Samples of the tape were immersed in 100 cc of boiling petroleum in a flask for 45 minutes. The solution was decanted off and replenished with 100 cc petroleum ether and boiled for a further 60 minutes. Substantially all of the polypropylene was extracted from the tape leaving a structure comprising spaced fibrils of polyurethane which were substantially aligned to the axis of the tape, such aligned spaced fibrils being interconnected to each other in a random manner.

The tape was white, opaque, integral, elastic and was ideally suited as a soft tissue substitute.

There are many cases in surgery where a synthetic alternative to soft tissue is desirable. Such cases occur in reconstructive surgery following trauma, in the need for a skin graft following thermal or chemical burns or in augmentation prosthesis. The degree to which natural tissue ingrowth into such a synthetic medium would be required, may be different in each case. This may vary from a very shallow penetration to complete incorporation or encapsulation of the substitute by new connective tissue.

The ability to manipulate fibril size and hence pore size of the medium will be of particular value in the design of such a substitute.

It is an additional requirement that the polymer does not provoke a foreign body reaction from the host. This requirement of biocompatibility may be taken to mean that the polymer is completely tolerated by its host or it may also be designed to be absorbed by the host over a period of time. If completely tolerated by the host, it would provide a biocompatable covering for materials of lower tolerance and, by promoting varying degrees of tissue ingrowth, may provide an anchorage for such materials in the body or a biologically sealed interface with the host such as in a percutaneous access device.

Many synthetic polymers have been screened and applied in the field such as sponges of polyurethane, polyhydroxyethylmethacrylate and polyvinylalcohol (Salvatore et al Surgery, Gynecology and Obstetrics 1961 112 463) with varying degrees of success.

Though the tape or film of the invention can be of any suitable fibre-forming polymer which is chemically inert and body and blood compatible, we prefer that it is of a melt-spinnable polyether based polyurethane. A particularly desirable polyether based polyurethane is one which is based on poly-(tetrahydrofuran), methylene bis (4-phenylisocyanate) and 1,4-butane diol and the suitability of such polyurethanes as materials for prosthesis are supported by D Annis et al in Vol XXIV Trans Am Soc Artif Intern organs. 1978 209. Other polyurethanes which may be used are those based on nydroxyl terminated polycarbonates and other glycol residues such as polyethyleneglycol which will introduce a degree of hydrophilicity to the tape or film.

Apart from the tape of film being of a polyurethane, we envisage that it could also be of such fibre forming polymers as polypropylene, polyethylene, polyester, fluoropolymers, polystyrene, polyvinylchloride, polymethylmethacrylate, cellulose acetate butyrate and polyhydroxy butyric acid.

Also, by careful selection of polymer the film or tape may be rendered biogradable which may be required.

It will be realised that though the polyurethane used in Example 2 is a member of the class of polyurethanes which we have said is particularly desirable, it should be understood that it is not necessarily biocompatible and in practice it would be necessary to use such a bicompatible polymer.

Furthermore it may be desirable at appropriate stages of the manufacturing process used to ensure that the soft tissue substitute has been sterilised as for example by the use of gamma radiation, and ethylene oxide gas.

Tapes and films according to the invention may also be used for a variety of other end uses including filtration or separation media.

Also if the tape or film is produced from a polymer which is biocompatible then they may be used as haemodialysis media.

We claim:

1. A self supporting melt spun film or tape of a fibre-forming polymer comprising spaced fibrils of the polymer which are substantially aligned to the longitudinal axis of the film or tape, such aligned, spaced fibrils being interconnected to each other in a random manner.

2. A self supporting melt spun film or tape as claimed in claim 1 in which the polymer contains aromatic repeat units in the chain and is selected from the group comprising polysulphones, polyethersulphones, polyetherethersulphones, polyetherketones, polyetheretherketones, polyarylene oxides, polyarylene sulphides, aromatic polyamides, aromatic polyesters, aromatic polycarbonates, polyetherimides.

* * * * *